US008790899B2

(12) United States Patent
Robison et al.

(10) Patent No.: US 8,790,899 B2
(45) Date of Patent: Jul. 29, 2014

(54) **REAL-TIME PCR ASSAYS FOR RAPID DETECTION AND DIFFERENTIATION OF THE *CLOSTRIDIUM BOTULINUM* TOXIN GENES A, B, E, AND F**

(76) Inventors: Richard A. Robison, Provo, UT (US);
David O. Pickett, Knoxville, TN (US);
Ben Satterfield, Webster, TX (US)

( * ) Notice: Subject to any disclaimer, the term of this patent is extended or adjusted under 35 U.S.C. 154(b) by 415 days.

(21) Appl. No.: 12/873,300

(22) Filed: Aug. 31, 2010

(65) Prior Publication Data

US 2012/0088680 A1 Apr. 12, 2012

Related U.S. Application Data

(60) Provisional application No. 61/275,789, filed on Sep. 1, 2009.

(51) Int. Cl.
*C12P 19/34* (2006.01)
(52) U.S. Cl.
USPC ........................................................ 435/91.2
(58) Field of Classification Search
USPC ........................................................ 435/91.2
See application file for complete search history.

(56) References Cited

FOREIGN PATENT DOCUMENTS

JP       2002-176982    *  6/2002
WO    WO 2008112177    *  9/2008

OTHER PUBLICATIONS

Akbulut et al., "Development and Application of Real-Time PCR Assays to Detect Fragments of the *Clostridium botulinum* Types A, B, and E Neurotoxin Genes for Investigation of Human Foodborne and Infant Botulism," Foodborn Pathogens and Disease, vol. 1, No. 4, (2004) 247-256.
Aranda, et al., "Detection of *Clostridium botulinum* types A, B, E and F in foods by PCR and DNA probe," Lett Appl Microbiol. Sep. 1997;25(3):186-90. (cited in spec as Aranda 1997).
Barash and Arnon, (2004), "Dual toxin-producing strain of *Clostridium botulinum* type Bf isolated from a California patient with infant botulism," J Clin Microbiol. Apr. 2004;42(4):1713-1715.
Bartram et al., "Infant Botulism and Sudden Infant Death Syndrome," Klin Padiatr 2004; 216: 26-30 (English Abstract).
Braconnier et al., "Screening for *Colostridium botulinum* Type A, B, and E in Cooked Chilled Foods Containing Vegetables and Raw Materials Using Polymerase Chain Reaction and Molecular Probes," Journal of Food Protection, vol. 64, No. 2, 2001, pp. 201-207.
Carter et al., "Independent evolution of neurotoxin and flagellar genetic loci in proteolytic *Clostridium botulinum*," BMC Genomics 2009 (10)115, 1-18.
Chen et al., "Sequencing the Botulinum Neurotoxin Gene and Related Genes in *Clostridium botulinum* Type E Strains Reveals orfx3 and a Novel Type E Neurotoxin Subtype," Journal of Bacteriology Dec. 2007, p. 8643-8650, vol. 189, No. 23.

Collins et al., "A Review Phylogeny and taxonomy of the food-borne pathogen *Clostridium botulinum* and its neurotoxins," Journal of Applied Microbiology 1998, 84, 5-17.
Cordoda et al., 1995J.J. Córdoba, M.D. Collins and A.K. East , Studies on the genes encoding botulinum neurotoxin type A of *C. botulinum* from a variety of sources. Syst. Appl. Microbiol. 18 (1995), pp. 13-22.
Dietmaier, et al., "Detection of Microsatellite Instability by Real Time PCR and Hybridization Probe Melting Point Analysis," Lab Invest 2001, 81:1453-1456.
Fach et al., "Detection by PCR—Enzyme-Linked Immunosorbent Assay of *Clostridium botulinum* in Fish and Environmental Samples from a Coastal Area in Northern France," Applied and Environmental Microbiology, Dec. 2002, p. 5870-5876 vol. 68, No. 12.
Fach et al., "Development of real-time PCR tests for detecting botulinum neurotoxins A, B, E, F producing *Clostridium botulinum*, *Clostridium baratii* and *Clostridium butyricum*," Journal of Applied Microbiology, 107 (2009) 465-473.
Fach et al., "PCR and Gene Probe Identification of Botulinum Neurotoxin A-, B-, E-, F-, and G-Producing *Clostridium spp.* and Evaluation in Food Samples," Applied and Environmental MicroBiology, Jan. 1995, p. 389-392.
Fach et al., "Polymerase chain reaction fot the rapid identification of *Colstridium botulinum* type A strains and detection in food samples," Journal of Applied Bacteriology, 1993, (75), 234-239.
Franciosa et al., "Detection of Type A, B, and E Botulism Neurotoxin Genes in *Clostridium botulinum* and Other *Clostridium* Species by PCR: Evidence of Unexpressed Type B Toxin Genes in Type A Toxigenic Organisms," Journal of Clinical Microbiology, Aug. 1994, vol. 32, No. 98, p. 1911-1917.
Franz et al., "Clinical Recognition and Management of Patients Exposed to Biological Warfare Agents," Special Communications, JAMA Aug. 6, 1997, vol. 278, No. 5, p. 399-411.
Gimenez et al., "Another Type of *Clostridium botulinum*," Zbl. Bakt., I. Abt. Orig. 215, 221-224 (1970).
Hatheway, Charles L., "Toxigenic Clostridia," Clinical Microbiology Reviews, Jan. 1990, vol. 3, No. 1, p. 66-98.
Heffron et al., "A PCR approach to determine the distribution of toxin genes in closely related *Clostridium* species: *Clostridium botulinum* type C and D neurotoxins and C2 toxin, and *Clostridium novyi* a toxin," Journal of Medical Microbiology (2007), 56, 196-201.
Hill et al., "Genetic Diversity among Botulinum Neurotoxin-Producing Clostridial Strains," Journal of Bacteriology, Feb. 2007, p. 818-832 vol. 189, No. 3.
Kasai et al., "Quantitative Duplex PCR of *Clostridium botulinum* Types A and B Neurotoxin Genes," J. Food Hyg. Soc. Japan vol. 48, No. 1, Feb. 2007, p. 19-26.
Kimura et al., "Rapid, Quantitative PCR Monitoring of Growth of *Clostridium botulinum* Type E in Modified-Atmosphere-Packaged Fish," Applied and Environmental Microbiology, Jan. 2001, p. 206-216.

(Continued)

*Primary Examiner* — Cynthia B Wilder
(74) *Attorney, Agent, or Firm* — Kunzler Law Group

(57) ABSTRACT

Provided herein is a method for detecting the presence or absence of at least one of *Clostridium botulinum* toxin gene A, B, E, and F in a biological sample by means of PCR amplification using toxin specific primers and labeled probes in connection with real time or delayed detection. Also provided are specific primer and probe sequences, a diagnostic method and a kit comprising primers and probes for detection of toxin genes A, B, E, or F in a biological sample.

27 Claims, 8 Drawing Sheets

(56) References Cited

OTHER PUBLICATIONS

Lindstrom et al., "Identification of *Clostridium botulinum* with API 20 A, Rapid ID 32 A and RapID ANA II," FEMS Immunology and Medical Microbiology 24 (1999) 267-274.

Lindstrom et al., "Multiplex PCR Assay for Detection and Identification of *Clostridium botulinum* Types A, B, E, and F in Food and Fecal Material," Applied and Environmental Microbiology, vol. 67, No. 12, Dec. 2001, p. 5694-5699.

Lyon, "Mutation detection using Fluorescent hbridization probes and melting curves analysis," Expert Rev Mol Diagn 1(1) 92-101 (2001).

Poumeyrol et al., "Intoxication botulique mortelle due a un souche de *Clostridium botulinum* de type AB*", Medicine et Maladies Infectieuses (1983) 13, N. 11, 750-754.

Prevot et al., "Optimization of Polymerase Chain Reaction for Detection of *Clostridium botulinum* Type C and D in Bovine Samples," Journal compilation 2007 Blackwell Verlag, Zoonoses Public Health. 54 (2007) 320-327.

Smith et al., "Analysis of the Neurotoxin Complex Genes in *Clostridium botulinum* A1-A4 and B1 Strains: BoNT/A3, / Ba4 and /B1 Clusters Are Located within Plasmids," PLoS One, Dec. 2007, e1271, p. 1-10.

Smith et al., "Sequence Variation within Botulinum Neurotoxin Serotypes Impacts Antibody Binding and Neutralization," Infection and Immunity, Sep. 2005, p. 5450-5457 vol. 73, No. 9.

Song et al., "Real-Time PCR Quantitation of Clostridia in Feces of Autistic Children," Applied and Environmental Microbiology, Nov. 2004, p. 6459-6465, vol. 70, No. 11.

Suen et al., "*Clostridiurn argentinense* sp. nov.: a Genetically Homogeneous Group Composed of All Strains of *Clostridium botulinum* Toxin Type G and Some Nontoxigenic Strains Previously Identified as *Clostridium subterminale* or *Clostridium hastiforme*," International Journal of Systematic Bacteriology, Oct. 1988, p. 375-381, vol. 38, No. 4.

Szabo et al., "Detection of the Genes Encoding Botulinum Neurotoxin Types A to E by the Polymerase Chain Reaction,"Applied and Environmental Microbiology, Sep. 1993, p. 3011-3020, vol. 59, No. 9.

Takeshi et al., "Simple Method for Detection of *Colstridium botulinum* Type A to F Neurotoxin Genes by Polymerase Chain Reaction," Micriobiol. Immunol., 40(1), May 2011, 1996.

Yoon et al., "Application of Real-Time PCR for Quantitative Detection of *Colstridium botulinum* Type A Toxin Gene in Food," Microbiol Immunol., 49(6)505-511, 2005.

Alsallami et al., "Selection of primers for specific detection of *Clostridium botulinum* types B and E neurotoxin genes using PCR method", International Journal of Food Microbiology, vol. 69, Issue 3, Sep. 2001, pp. 247-253.

Satterfield et al., "A quadruplex real-time PCR assay for rapid detection and differentiation of the *Clostridium botulinum* toxin genes A, B, E and F", Journal of Medical Microbiology (2010), 59, pp. 55-64.

* cited by examiner (a)

(b)

```
                         SEQUENCE LISTING

<160> NUMBER OF SEQ ID NOS: 12

<210> SEQ ID NO 1
<211> LENGTH: 25
<212> TYPE: DNA
<213> ORGANISM: Clostridium botulinum

<400> SEQUENCE: 1
acgcgaaatg gttatggytc tactc                                           25

<210> SEQ ID NO 2
<211> LENGTH: 24
<212> TYPE: DNA
<213> ORGANISM: Clostridium botulinum

<400> SEQUENCE: 2
gtgctaatgy tacygctgga tctg                                            24

<210> SEQ ID NO 3
<211> LENGTH: 24
<212> TYPE: DNA
<213> ORGANISM: Clostridium botulinum

<400> SEQUENCE: 3
```
agtaatccag gagaagtgga gcga                                          24

<210> SEQ ID NO 4
<211> LENGTH: 22
<212> TYPE: DNA
<213> ORGANISM: Clostridium botulinum

<400> SEQUENCE: 4
craagccttc ccttgatgca aa                                            22

<210> SEQ ID NO 5
<211> LENGTH: 24
<212> TYPE: DNA
<213> ORGANISM: Clostridium botulinum

<400> SEQUENCE: 5
cacagaaagt gcccgaaggt gaaa                                          24

<210> SEQ ID NO 6
<211> LENGTH: 24
<212> TYPE: DNA
<213> ORGANISM: Clostridium botulinum

<400> SEQUENCE: 6
gctgcttgca caggtttatt gaca                                          24

<210> SEQ ID NO 7
<211> LENGTH: 25
<212> TYPE: DNA
<213> ORGANISM: Clostridium botulinum

<400> SEQUENCE: 7
gtggagggma tmatagtagt acaga                                         25

<210> SEQ ID NO 8
<211> LENGTH: 25
<212> TYPE: DNA
<213> ORGANISM: Clostridium botulinum

<400> SEQUENCE: 8
ggctatcata agaggtscty gcttt                                         25

<210> SEQ ID NO 9
<211> LENGTH: 30
<212> TYPE: DNA
<213> ORGANISM: Clostridium botulinum

<400> SEQUENCE: 9
tgaggagtca cttgaagttg atacaaatcc                                    30

<210> SEQ ID NO 10
<211> LENGTH: 30
<212> TYPE: DNA
<213> ORGANISM: Clostridium botulinum

<400> SEQUENCE: 10
cgcaaattta ataatatttg gacctgggcc                                    30

<210> SEQ ID NO 11
<211> LENGTH: 30
<212> TYPE: DNA
<213> ORGANISM: Clostridium botulinum

<400> SEQUENCE: 11

```
gtcaatctca cctcttcaat tgatacagca                                              30

<210> SEQ ID NO 12
<211> LENGTH: 27
<212> TYPE: DNA
<213> ORGANISM: Clostridium botulinum

<400> SEQUENCE: 12
agctcatgaa ttgatacatg cactgca                                                 27
```

US 8,790,899 B2

REAL-TIME PCR ASSAYS FOR RAPID DETECTION AND DIFFERENTIATION OF THE *CLOSTRIDIUM BOTULINUM* TOXIN GENES A, B, E, AND F

CROSS-REFERENCES TO RELATED APPLICATION

This patent application claims the benefit of U.S. Provisional Patent Application No. 61/275,789 filed on 1 Sep. 2009, entitled "A QUADRAPLEXED REAL-TIME PCR ASSAY FOR RAPID DETECTION AND DIFFERENTIATION OF THE CLOSTRIDIUM BOTULINUM TOXIN GENES A, B, E, AND F," naming Richard A. Robison, David O. Pickett, and Ben Satterfield as inventors. The content and subject matter of this patent application is hereby incorporated by reference in its entirety, including all text and drawings.

FIELD OF THE INVENTION

The method provided herein relates to the field of genetic assays and more particularly to genetic assays for botulinum toxin. This specification incorporates by reference the material in the file that is named BYU-0100-UT_Seq-ID-Lst_Aug0111-ST25.txt, was created on Aug. 1, 2011, and was uploaded to the USPTO's EFS website on Aug. 1, 2011. The content of the sequence listing information recorded in computer readable form is identical to the written sequence listed in the application as filed and includes no new matter.

BACKGROUND

*Clostridium botulinum* (*C. botulinum*) is the etiologic agent of botulism, a disease marked by flaccid paralysis that can progress to asphyxiation and death. This species is defined by the production of one of the botulinum neurotoxins (BoNTs) which are the most potent toxins known. Because of their potency, these toxins have the potential to be used as biological weapons, and therefore, *C. botulinum* has been classified as a category A select agent. There are four related but antigenically distinct BoNT types that cause disease in humans, (A, B, E, and F). Various assays and detection protocols have been used to identify BoNT in various substances, including food, animal tissue, and fecal samples (Dietmaier & Hofstadter, 2001; Franz et al., 1997; Lyon et al., 2001). The mouse bioassay is the current gold standard by which BoNTs is confirmed. However, this method is expensive, slow, and very labor intensive.

SUMMARY

Provided herein is a method for detecting the presence or absence of at least one of *Clostridium botulinum* toxin genes A, B, E, and F in a biological sample. In some embodiments the method comprises preparing a nucleic acid mixture comprising (i) DNA from the biological sample; (ii) at least one polynucleic acid primer pair selected from the group consisting of sequences having at least 90% homology to the sequences of SEQ ID NOs: 1-2, 3-4, 5-6, and 7-8; and (iii) at least one polynucleic acid probe selected from the group consisting of sequences having at least 90% homology to the sequences of SEQ ID NOs 9, 10, 11, and 12, wherein each probe is labeled with a different detectable label. In such embodiments the method further comprises conducting an amplification reaction with a DNA polymerase using the mixture and detecting hybridization of any of at least one probe to the amplification product in either real time or delayed time. Hybridization indicates the presence of at least one of toxin genes A, B, E, or F in the biological sample.

In some embodiments the amplification reaction is a multiplex reaction. In various embodiments the detectable label is a fluorescent label. In certain embodiments the detectable label is selected from the group consisting of FAM, Cy3, Cy5 and Texas Red (TexR). A signal from at least two detectable labels is sometimes displayed simultaneously on at least two optical channels.

In some embodiments the sample is from a mammal. The sample may be selected from the group consisting of serum, emesis, wound, tissue, blood, and stool samples. The sample is sometimes from a human.

In certain embodiments the sample is vegetative matter. In some embodiments the sample is one of a food product or medicant suitable for ingestion by an animal or a human. The sample may sometimes come from a public food supply and the method may sometimes comprise issuing a public health advisory based on the results of the assay method.

Also provided is a method of diagnosing *C. botulinum* in a human comprising determining the presence or absence of a *C. botulinum* toxin gene in a sample from the human according claim 1, and correlating the presence or absence of *C. botulinum* toxin gene in the sample with the diagnosis of the human as being or not being infected or intoxicated with *C. botulinum*. In some embodiments the method comprises administering an anti-toxin against the toxin produced by the toxin gene identified.

Provided herein are isolated polynucleic acid primers having least 90% homology to the sequence ACGCGAAATG-GTTATGGYTCTACTC (SEQ ID NO:1), GTGCTAAT-GYTACYGCTGGATCTG (SEQ ID NO:2), AGTAATCCAGGAGAAGTGGAGCGA (SEQ ID NO:3), CRAAGCCTTCCCTTGATGCAAA (SEQ ID NO:4), CACAGAAAGTGCCCGAAGGTGAAA (SEQ ID NO:5), GCTGCTTGCACAGGTTTATTGACA (SEQ ID NO:6), GTGGAGGGMATMATAGTAGTACAGA (SEQ ID NO:7), and GGCTATCATAAGAGGTSCTYGCTTT (SEQ ID NO:8).

Also provided are isolated polynucleic acid probes having at least 90% homology to TGAGGAGTCACTTGAAGT-TGATACAAATCC (SEQ ID NO:9), CGCAAATT-TAATAATATTTGGACCTGGGCC (SEQ ID NO:10), GTCAATCTCACCTCTTCAATTGATACAGCA (SEQ ID NO:11), and AGCTCATGAATTGATACATGCACTGCA (SEQ ID NO:12).

Herein provided is a kit for detecting the presence of at least one of *Clostridium botulinum* toxin genes A, B, E, and F in a biological sample. In certain embodiments the kit comprises at least one polynucleic acid pair for use as primers selected from the group consisting of SEQ ID NOs: 1-2, 3-4, 5-6, and 7-8; and at least one polynucleic acid selected from the group consisting of SEQ ID NOs 9, 10, 11, and 12 for use as probes, with each probe labeled with a different detectable label. The kit sometimes comprises instructions for use and may comprise reaction reagents.

*perfringens*, hatched) produced negative results. CT values are expressed as vertical lines and the threshold is expressed as a horizontal line.

FIG. 2 depicts sensitivity of the singleplex assays. Standard curves were derived from tenfold dilutions of purified genomic DNAs for *C. botulinum* isolates containing the toxin genes for toxin A (a), toxin B (b), toxin E (c) and toxin F (d). Initial concentration, solid line; first tenfold dilution, long dash; second tenfold dilution, medium dash; third tenfold dilution, short dash; fourth tenfold dilution dotted; fifth tenfold dilution long dash-short dash.

FIG. 3 depicts the sensitivity of the quadruplex assay, e.g. primers and probes for all toxin types and subtypes were added to the reaction for each toxin type. Standard curves were derived from tenfold dilutions of purified genomic DNAs for *C. botulinum* isolates containing the toxin genes for toxin A (a), toxin B (b), toxin E (c) and toxin F (d). Dilutions were as described for FIG. 2.

FIG. 4 depicts detection of the presence of toxin genes in environmental samples. Detection of toxin A (a), toxin B (b), toxin E (c) and toxin F (d) after DNA was extracted from environmental samples inoculated with *C. botulinum*. Samples tested included genomic DNA control (short dash), sausage (medium dash), vegetable matter (solid), soil (long dash) and a no-template control (dotted).

Figure 5A:
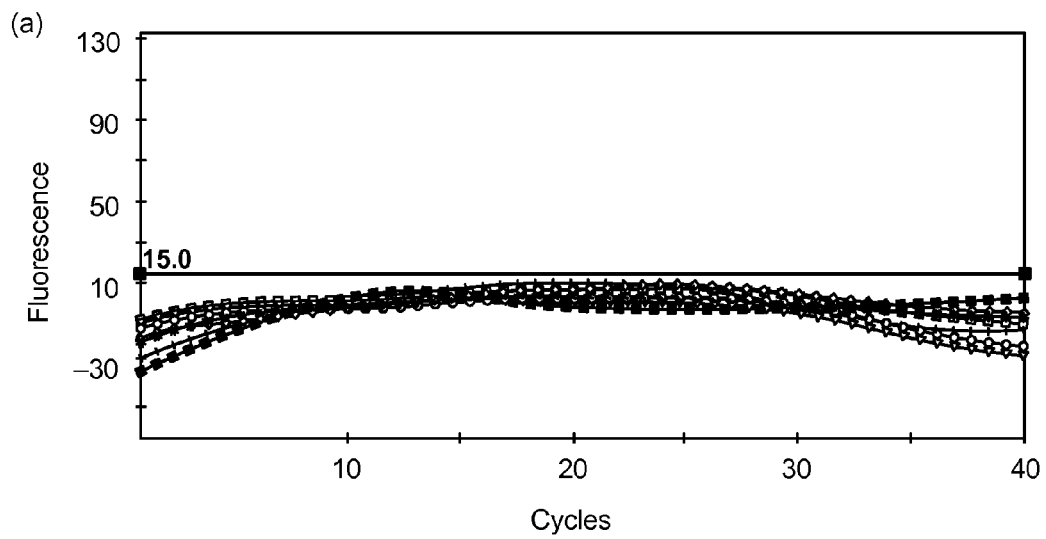
Figure 5B:
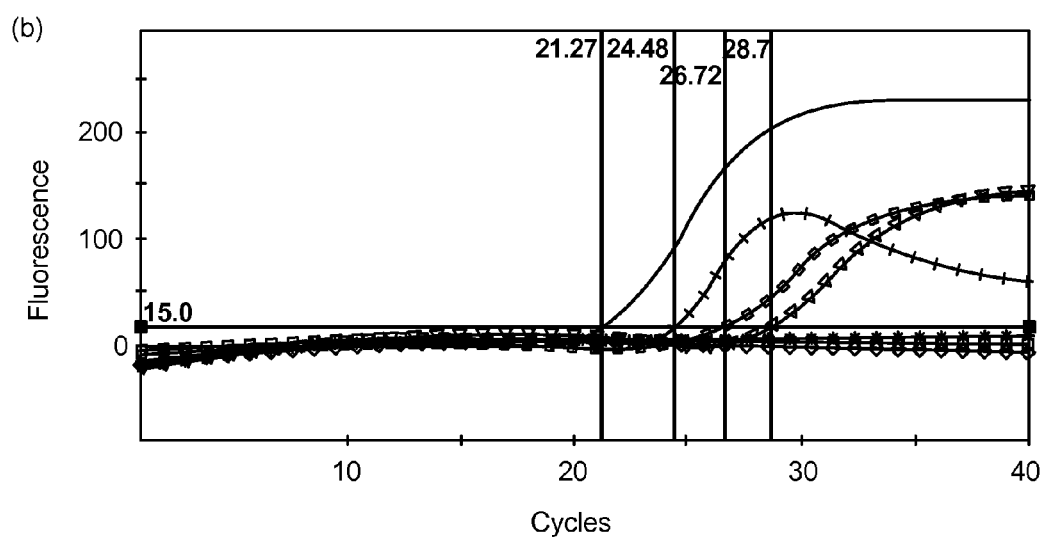

FIG. 5 depicts detection of the presence of toxin genes in fecal samples. (a) Tests for toxin A (solid), toxin B (+), toxin E (square), and toxin F (*) performed after DNA was extracted from fecal samples inoculated with *C. botulinum* gave negative results. (b) The same as (a) except that purified DNA of the respective toxin type was spiked into each fecal extraction sample, producing a positive test result and indicating that the previous negative result arose from the DNA extraction process rather than the type-specific DNA test.

DETAILED DESCRIPTION

Provided herein is a qPCR single-tube assay that uniquely identifies the four BoNT types A, B, E, and F responsible for human disease.

In certain embodiments as provided herein, all the primers, probes, and target DNA are loaded into a single tube. Each individual dual-labeled hydrolysis probe has a unique fluorescence signal, which may be detected and analyzed by the specific detection channels of, for example, the SmartCycler II. In some embodiments each primer is specific for DNA sequences corresponding to a particular toxin type. In various embodiments, these components comprise an assay capable of specifically detecting genes for from one to all four toxin types within a single PCR tube.

In some embodiments, the quadraplexed qPCR assay provided herein can detect all human disease-causing BoNTs, even if all four are present in the same sample. The quadraplexed assay can detect as few as 15-100 genome copies depending on the toxin type, and is robust enough to function in the presence of extracted organic material and soil. In certain embodiments the assay is conducted with one or more primer sets and probes configured to detect one or more toxin gene. Such an assay could be a rapid, sensitive, and economical tool in the detection of BoNT-producing organisms present in a wide variety of samples, and provide researchers and clinicians with a rapid and reliable means of determining BoNT type.

Definitions

The term "method" as used herein refers to the method, assay, kit, and other method provided herein.

The term "polynucleic acid" as used herein refers to a short polymer composed of deoxyribonucleotides, ribonucleotides, or a mixed polymer of each. These polynucleic acids are at least 9 nucleotides in length, sometimes 20 to 70 nucleotides long, and may be 21 to 26 nucleotides long. In certain embodiments, the polynucleic acids are chemically linked or otherwise associated with a detectable label.

The standard notations G (guanine), C (cytosine), A (adenosine), and T (thymine) are used to designate nucleotides in polynucleic acid sequences. In cases where one of two nucleotides may occupy a given position R is used to designate either A or G (purine), Y is used to designate either T or C (pyrimidine), and M is used to designate either A or C.

The term "isolated" as used herein with reference to a nucleic acid (e.g., an RNA, DNA or a mixed polymer) refers to one that is substantially separated from other cellular components that naturally accompany such nucleic acid. The term embraces a nucleic acid sequence that has been removed from its naturally occurring environment, and includes recombinant or cloned DNA isolates, polynucleic acids, and chemically synthesized analogs or analogs biologically synthesized by heterologous systems.

The term "primer" as used herein means a sequence of nucleic acid, preferably DNA, which hybridizes to a substantially complementary target sequence and is recognized by DNA polymerase to begin DNA replication. A primer herein may have a DNA sequence from 90% to 100% homologous to those provided. In various embodiments the primer is 90%, 91%, 92%, 93%, 94%, 95%, 96%, 97%, 98%, 99%, or 100% homologous to the primers of SEQ ID NOs 1-8 provided herein.

The term "hybridize" as used herein refers to the process by which two complementary nucleic acid strands anneal to each other under appropriately stringent conditions. Hybridizations may be conducted with probe-length nucleic acid molecules, sometimes 20-100 nucleotides in length. Nucleic acid hybridization techniques are known in the art. Those skilled in the art understand how to estimate and adjust the stringency of hybridization conditions such that sequences having at least a desired level of complementarity will stably hybridize, while those having lower complementarity will not.

The term "complement" as used herein means the complementary sequence to a nucleic acid according to standard Watson/Crick pairing rules. A complement sequence can also be a sequence of RNA complementary to the DNA sequence or its complement sequence, and can also be a cDNA.

The term "probe" as used herein means a sequence of nucleic acids complementary and capable of hybridizing to a region of a target sequence. In some embodiments the probe comprises a label. A probe herein may have a DNA sequence from 90% to 100% homologous to those provided. In some embodiments the primer is 90%, 91%, 92%, 93%, 94%, 95%, 96%, 97%, 98%, 99%, or 100% homologous to the probes of SEQ ID NOs 9-12 provided herein.

The term "amplification" or "amplify" as used herein means one or more methods known in the art for copying a target nucleic acid, thereby increasing the number of copies of a selected nucleic acid sequence. Amplification may be exponential or linear. A target nucleic acid may be either DNA or RNA. The sequences amplified in this manner form an "amplicon." While the exemplary methods described hereinafter relate to amplification using the polymerase chain reaction ("PCR"), numerous other methods are known in the art for amplification of nucleic acids (e.g., isothermal methods, rolling circle methods, etc.). The skilled artisan will understand that these other methods may be used either in place of, or together with, PCR methods.

The terms "real time PCR," "quantitative PCR," or "qPCR" as used herein mean that a signal emitted from the PCR assay is monitored during the reaction as an indicator of amplicon production during each PCR amplification cycle (i.e., in "real time"), as opposed to conventional PCR methods, in which an assay signal is detected at the endpoint of the PCR reaction. Real time PCR is generally based on the detection and quantitation of a fluorescent reporter. The signal increases in direct proportion to the amount of PCR product in a reaction. By recording the amount of fluorescence emission at each cycle, it is possible to monitor the PCR reaction during exponential phase where the first significant increase in the amount of PCR product correlates to the initial amount of target template. Various PCR methods enable real-time, kinetic quantification measurements to be made during the log-linear phase of a PCR.

The term "multiplex PCR" refers to the use of more than one set of PCR primers, resulting in the amplification of more than one DNA sequence. The term "quadraplexed PCR" as used herein refers to a multiplex PCR using four sets of primers and probes.

One general method for real time PCR uses fluorescent probes including but not limited to the TaqMan® probes, molecular beacons and scorpions. Real-time reverse-transcriptase (RT) PCR may quantitate the initial amount of the template with more specificity, sensitivity and reproducibility, than other forms of quantitative reverse transcriptase PCR, which detect the amount of final amplified product.

Botulism

*Clostridium botulinum* is a spore-forming, gram-positive bacterium that produces the most potent toxins known with a $LD_{50}$ in primates of 1-10 ng (kg of body weight)$^{-1}$ (Franz et. al., 1997). Due to their potency, BoNTs have the potential to be used as biological weapons. Therefore, *C. botulinum* has been classified as a category A select agent by the CDC. BoNTs can enter the body via three different routes: inhalation, ingestion, and absorption from wound infections. Ingestion of *C. botulinum* spores by infants has been associated with sudden infant death syndrome (Bartram & Singer, 2004; Smith & Sugiyama, 1988). Once vegetative cells are lysed, the toxin is released (Franz et al., 1997) and, upon entering a mammalian host, the toxin is taken up by lower motor neurons at the neuromuscular junction. The toxin acts to block acetylcholine release by cleaving the SNARE proteins, thus blocking neurotransmitter exocytosis. This creates a state of flaccid paralysis in the affected individual that steadily increases until asphyxiation and death. This paralytic disease state is known as botulism.

The defining characteristic of the genetically diverse *C. botulinum* species is the production of one or more of the seven antigenically distinct BoNTs: A, B, C, D, E, F, or G (Collins & East, 1998; Hatheway, 1990; Lindstrom et al., 2001). Human botulism is caused typically by toxin types A, B, E, and occasionally F. BoNT genes from numerous strains of types A, B, E and F have been sequenced and have shown 2.6-31.6% sequence variation within each serotype (Smith et al., 2005). This has led to the identification of various subtypes within each toxin type: five distinct subtypes within the BoNT A serotype (Carter et al., 2009), four or five subtypes within the BoNT B serotypes (Hill et al., 2007; Smith et al., 2007), six distinct subtypes of serotype E strains (Chen et al., 2007) and three subtypes of BoNT F (Smith et al., 2005).

The detection and identification of *C. botulinum* is useful to researchers, food processors, and health care professionals. The mouse bioassay is expensive, slow, and very labor intensive, taking up to four days to complete. In addition, this assay carries ethical concerns due to the need to sacrifice mice. Commercial biochemical tests have failed in identifying various toxin-producing strains of *C. botulinum* (Lindstrom et al., 1999). PCR-based assays have been used extensively for detection of BoNTs in food, animals, and fecal samples (Aranda et al., 1997; Braconnier et al., 2001; Dietmaier & Hofstadter, 2001; Fach et al., 1993; Fach et al., 1995; Fach et al., 2002; Franciosa et al., 1994; Lindstrom et al., 2001; Takeshi et al., 1996). Traditional PCR methods using agarose gel electrophoresis for the characterization of amplification products can be used (Szabo et al., 1993), but require more time to perform because of the added step of gel electrophoresis, and the identification is based solely on the size of the amplicons, which may be misleading. qPCR overcomes these deficiencies by using a combination of primers and fluorescent probes specific for a unique DNA sequence. The detection of the target product is followed in real-time as the reaction occurs without the need for agarose gel electrophoresis. Yoon et al. (2005), Kimura et al. (2001) and Fach et al. (2009) used real-time based assays to target single botulinum toxin genes, while Akbulut et al. (2004) and Kasai et al. (2007) targeted multiple BoNT genes in a single real-time reaction. The single target assays do not completely provide researchers or clinical laboratory technicians the ability to identify which BoNT gene is present in an isolate.

Botulism Toxins

*C. botulinum* strains are not as homogenous as many other bacterial species; they have marked genotypic heterogeneity and express varied phenotypical characteristics such as optimal growth temperatures (ranging from 18° C. to 40° C.), biochemical profiles, and metabolite production. There are also non-BoNT producing strains that are so closely related that they can be genetically and biochemically identified as members of each *C. botulinum* group (Collins & East, 1998; Hatheway, 1990; Lindstrom et al., 2001) but are given different species names because they produce no toxin. The main commonality between all *C. botulinum* strains is the production of one or more of the seven antigenically distinct BoNTs: A, B, C, D, E, F, or G (Collins & East, 1998; Hatheway, 1990; Lindström et al., 2001). *C. botulinum* strains can be divided into four groups (I-IV) depending on which toxin type(s) the organism produces, with groups I and II being the primary cause of disease in humans. Group I consists of any strain producing one or more of the following toxin types: A and the proteolytic types B and F. Group II consists of any strain producing one or more of the following toxin types: E and the nonproteolytic types B and F. Group III organisms produce toxin types C and D (Collins & East, 1998; Lindstrom et al., 2001; Smith & Sugiyama, 1988), which often cause botulism in birds and cattle (Heffron & Poxton, 2007; Prévot et al., 2007). Group IV organisms produce toxin type G (Collins & East, 1998; Smith & Sugiyama, 1988), which has not been shown to produce disease in animals or humans (Yoon et al., 2005). *C. botulinum* isolates that produce the G toxin are classified by some as their own species, *Clostridium argentinense* (Suen et al., 1988).

While most *C. botulinum* strains produce a single BoNT, there have been some isolates identified that produce a mixture of two toxin types: A and F (Giménez & Ciccarelli, 1970), A and B (Cordoba et al., 1995; Poumeyrol et al., 1983), and B and F (Barash & Amon, 2004; Hatheway & McCroskey, 1989). Some type A isolates have been found to harbor silent type B BoNT genes (Cordoba et al., 1995; Franciosa et al., 1994). When multiple toxin genes are present, the primary toxin produced is usually dependent on growth temperature (Barash & Amon, 2004).

The method provided herein may be used to identify *C. botulinum* toxin genes A, B, D, and F in a variety of samples including without limitation soil, foods, medicines, and samples extracted from mammals and other living organisms. Identification of toxin genes in a public food supply may enable a timely public health advisory. Identification of toxin genes in, for example, a sample from a human, may contribute to diagnosis of botulism toxicity and may reveal the identity of the specific toxin or toxins. The sample may be taken from, without limitation, any body tissue, fluid, emission, digestive content, or secretion and may be obtained through swabbing, curettage, excision, hypodermic extraction, scraping, and other applicable technique.

In some embodiments the method further comprises treatment with one or more botulism anti-toxins specific for toxin A, B, E or F. The anti-toxin may be formulated as, for non-limiting example, an injection, an ingestible liquid, syrup, tablet, capsule, bolus, or delayed release capsule, a topical liquid, cream, or lotion, and an aerosol. Anti-toxin may be administered through any convenient technique, including ingestion, injection, bolus, transfusion, enema, suppository, topical application, and inhalation.

Reference throughout this specification to "some embodiments," "certain embodiments," or similar language means that a particular feature, structure, or characteristic described in connection with the embodiment is included in at least one embodiment of the present method. Thus, appearances of the phrases "in some embodiments," "in certain embodiments," and similar language throughout this specification may, but do not necessarily, all refer to the same embodiment.

Furthermore, the described features, structures, or characteristics of the method may be combined in any suitable manner in one or more embodiments. In the following description, numerous specific details are provided. One skilled in the relevant art will recognize, however, that the method can be practiced without one or more of the specific details, or with other methods, components, materials, and so forth. In other instances, structures, materials, or operations that are known in the art are not shown or described in detail to avoid obscuring aspects of the method provided herein.

The method herein may be embodied in other specific forms without departing from its spirit or essential characteristics. These features and characteristics of the present method will become more fully apparent from the following description and appended claims, or may be learned by the practice of the method as set forth hereinafter.

The described embodiments are to be considered in all respects only as illustrative and not restrictive. The scope of the method is, therefore, indicated by the appended claims rather than by the foregoing description. All changes that come within the meaning and range of equivalency of the claims are to be embraced within their scope.

The following examples serve to illustrate the present method. These examples are in no way intended to limit the scope of the method.

EXAMPLES

Example 1

Evaluation of Botulinum Isolates

A qPCR single-tube assay was developed that uniquely identifies the four BoNTs responsible for human disease. A total of 79 C. botulinum isolates with varying toxin types were evaluated, as well as numerous near-neighbors and other bacterial species. Included were isolates possessing genes for each of the toxins A, B, E, and F with some wild isolates containing genes for more than one BoNT. Results showed that this quadraplexed assay was capable of detecting any of the four BoNT genes in a given sample at a sensitivity of as little as 130 fg of genomic DNA, or of about 130-840 fg of genomic DNA and could detect the presence of two, three and up to all four BoNT genes simultaneously in a given sample (even though the existence of a strain producing more than two BoNT types has not been described), indicating the lack of type-to-type interference. The assay was also functional in the presence of extraneous organic matter commonly found in various environmental samples Example 2

Bacterial Isolates and Culture Conditions

Bacterial isolates (Supplementary Table 1) used in this study were acquired from ATCC, the CDC, and the UDH. Isolates were inoculated on Reinforced Clostridial Agar (RCA) and grown in an anaerobic chamber at 37° C. for 3-5 days prior to DNA extraction.

Example 3

DNA Extraction

Total genomic DNA was extracted from each isolate by first suspending cells grown on RCA plates in 250 µL of Tris/EDTA buffer [10 mM Tris/HCl (pH 8.0), 1 mM EDTA] (TE buffer) containing 1.8 µg lysozyme µL-1 and incubated for 1 h at 37° C. To this tube, 270 µL of bacterial lysis buffer and 100 µL of proteinase K were added and the tube was incubated for 10 min at 65° C. Samples were then incubated in boiling water for 10 min followed by an automated DNA extraction performed with a Roche MagNA Pure LC system (Roche Diagnostics) using the Roche MagNA Pure LC DNA Isolation Kit III as recommended by the manufacturer. DNAs were diluted with TE buffer in preparation for filtering, and stored at 4° C. overnight, followed by filtering with a 0.2 µm centrifuge filter and then tested for sterility. DNA concentrations were measured using a TBS-380 Fluorometer (Tuner Biosystems) and a PicoGreen kit P7589 (Invitrogen).

Example 4

Primer and Probe Design

DNA sequences for isolates from each subtype of the C. botulinum A, B, E and F toxin genes were obtained from GenBank (Table 1). All primers and 5'-hydrolysis dual-labeled probes (Table 2) were designed using the PrimerQuest algorithms from Integrated DNA Technologies (www.idtdna.com/Scitools/Applications/Primerquest/). Primer sequences were selected for proper GC content, optimal annealing temperatures, and lack of hairpin structures. A thorough BLAST search was performed to ensure both primer and probe specificity and lack of homology with sequences from other organisms and toxins. Probes were fluorescently labeled as follows: toxin A FAM, toxin B Cy3, toxin E Cy5 and toxin F Texas Red (TexR). Primer and probe sequences were chosen that would allow amplification of all subtypes, with the possible exception of the rare subtype E6.

TABLE 1

BoNT subtype accession numbers used for primer development

| BoNT Subtype | C. botulinum Strain | Accession Number | Reference |
|---|---|---|---|
| A1 | ATCC 25763 | EF028391 | Hill et al., 2007 |
| A2 | Kyoto-F | X73423 | Arndt et al., 2006 |
| A3 | Lach Maree | DQ185900 | Arndt et al., 2006 |
| A4 | 657 | DQ185901 | Arndt et al., 2006 |
| A5 | H0 4402 065 | EU679004 | Carter et al., 2009 |
| B-bivalent (BvB) | 657 | EF033130 | Smith et al., 2007 |
| B1 | CDC 1758 | EF033127 | Hill et al., 2007 |
| B2 | ATCC 7949 | EF028395 | Hill et al., 2007 |
| B3 | CDC 795 | EF028400 | Hill et al., 2007 |
| B-nonproteolytic | ATCC 25765 | X71343 | Hill et al., 2007 |
| E1 | K14 | AM695757 | Chen et al., 2007 |
| E2 | E544 | EF028404 | Chen et al., 2007 |
| E3 | E185 | EF028403 | Chen et al., 2007 |
| E4 | C. butyricum BL6340 | AB039264 | Chen et al., 2007 |
| E5 | C. butyricum LCL155 | AB037704 | Chen et al., 2007 |
| E6 | K35 | AM695752 | Chen et al., 2007 |
| F-proteolytic | NCTC 10281 | X81714 | Smith et al., 2005 |
| F-nonproteolytic | ATCC 23387 | M92906 | Smith et al., 2005 |
| F-bivalent (BvF) | CDC 3281 | Y13631 | Smith et al., 2005 |

TABLE 2

Primer and probe sequences

| Target (gene) | Primer/Probe | Sequence (5' → 3') | Amplicon Size (bp) |
|---|---|---|---|
| Toxin A | Forward | ACGCGAAATGGTTATGGYTCTACTC (SEQ ID NO. 1) | 142 |
| | Reverse | GTGCTAATGYTACYGCTGGATCTG (SEQ ID NO. 2) | |
| | Probe: | FAM-TGAGGAGTCACTTGAAGTTGATACAAATCC-(SEQ ID NO. 9) BHQ1 | |
| Toxin B | Forward | AGTAATCCAGGAGAAGTGGAGCGA (SEQ ID NO. 3) | 136 |
| | Reverse | CRAAGCCTTCCCTTGATGCAAA (SEQ ID NO. 4) | |
| | Probe: | Cy3-CGCAAATTTAATAATATTTGGACCTGGGCC-(SEQ ID NO. 10) IabRQ | |
| Toxin E | Forward | CACAGAAAGTGCCCGAAGGTGAAA (SEQ ID NO. 5) | 136 |
| | Reverse | GCTGCTTGCACAGGTTTATTGACA (SEQ ID NO. 6) | |
| | Probe: | Cy5-GTCAATCTCACCTCTTCAATTGATACAGCA-(SEQ ID NO. 11) BHQ2 | |
| Toxin F | Forward | GTGGAGGGMATMATAGTAGTACAGA (SEQ ID NO. 7) | 155 |
| | Reverse | GGCTATCATAAGAGGTSCTYGCTTT (SEQ ID NO. 8) | |
| | Probe: | TexR-AGCTCATGAATTGATACATGCACTGCA-BHQ2 (SEQ ID NO. 12) | |

BHQ1, Black Hole Quencher 1; IabRQ, Iowa Black Quencher RQ; BHQ2, Black Hole Quencher 2

Example 5 qPCR Optimization

Parameter variables such as the number of PCR cycles, cycle temperatures, and length of annealing and replicating steps, were all optimized. Primers were first evaluated with SYBR Green to optimize cycle temperatures and times. For every two reactions, a master mix of 50 µL was prepared using SmartMix HM 50 µL beads and the following: forward primer at 500 nM, reverse primer at 500 nM, target DNA, 2 µL SYBR Green at a 25× concentration and HPLC H20 to 50 µL. The master mix was equally split between two 25 µL Cepheid PCR tubes, which were loaded into a SmartCycler II (Cepheid). During the cycling phase, the extension temperatures were varied from 52° C. to 66° C. in single degree increments to maximize the reaction. The optimized protocol identified and used for all singleplex assays was an initial denaturization at 95° C. for 120 s followed by 40 cycles of 95° C. for 15 s, then 62° C. for 30 s and 72° C. for 20 s.

Example 6

Quadraplexing the qPCR Assay

Once the single reaction conditions were optimized, the mixture was quadraplexed by using GE Healthcare Hot Start Mix RTG Master Mix (GE Healthcare). Sample volume was 25 µL per reaction as recommended by the manufacturers. For each reaction one master mix bead was added to a mixture of 250 nM of each primer and probe for toxin A and 500 nM of each primer and probe for toxins B, E, and F. Target DNA and PCR-grade H20 were added for a total reaction volume of 25 µL. If DNA containing genes from more than two different toxin types was used, two master mix beads were used per reaction. Thermal cycling conditions were the same as for the singleplex reactions. SmartCycler program conditions were the same as the program defaults. A sample was determined to be positive if it crossed a fluorescence threshold of 15 before cycle 40 (a CT value of less than 40). The Cepheid software allowed four optics channels to be monitored in real-time simultaneously. DNA from near neighbors and no template were used as negative controls. The optimized real-time protocol was evaluated using a collection of 79 *C. botulinum* isolates, six near neighbors, and 11 other common laboratory strains of bacteria

TABLE 3

Summary of quadraplexed qPCR results

| Toxin | A | B | E | F | A & B | B & F | A & E | No Tox. | C* | D* | Tot |
|---|---|---|---|---|---|---|---|---|---|---|---|
| C. botulinum | 36 | 14 | 5 | 4 | 7 | 2 | 2 | 1 | 9 | 3 | 81 |
| C. argentinense | 0 | 0 | 0 | 0 | — | — |  |  | — | — | 2 |
| C. beijernckii | 0 | 0 | 0 | 0 | — | — |  |  | — | — | 1 |
| C. haemolyticum | 0 | 0 | 0 | 0 | — | — |  |  | — | — | 1 |
| C. perfringens | 0 | 0 | 0 | 0 | — | — |  |  | — | — | 1 |
| C. subterminale | 0 | 0 | 0 | 0 | — | — |  |  | — | — | 1 |

*Purported isolates

Example 7

Environmental Samples

To examine the utility of this assay in investigating environmental samples or samples likely encountered in a natural disease outbreak, soil, vegetable material, sausage, and fecal material were each inoculated with *C. botulinum* cultures. Accordingly, 400 mg of sausage, 400 mg of vegetable matter (Beech Nut® Mixed Vegetables Baby Food), 150 mg of soil, and 150 mg of human feces were inoculated individually with 100 μL of concentrated (about 108 CFUs mL-1) cultures of *C. botulinum* isolates known to contain the A, B, E, and F toxin genes. Phase microscopy showed these cultures to be about 60% spores and 40% vegetative cells. For negative controls, concentrated cultures of individual isolates containing the C or D toxin genes or 100 μL of TE buffer (no bacteria) were used. After the inoculation, the suspensions underwent bead-beating for 5 minutes at the maximum setting in a Mini BeadBeater-8 (BioSpec Products) followed by an incubation for 30 min at 37° C. Samples were centrifuged for 5 min at 8 000 RPM. The supernatant was removed and 270 μL of bacterial lysis buffer and 100 μL of proteinase K were added followed by incubation at 65° C. for 10 min. Samples were then incubated in boiling water for 10 min followed by DNA extraction and dilution as described above. The extracted DNAs were then interrogated using the quadraplexed assay.

DNA extracted from each environmental sample was interrogated with the quadraplexed assay. It was found that the assay could differentiate between toxin types in the vegetable matter and the sausage with the negative controls (uninoculated and those inoculated with isolates producing toxin types C or D) showing no signal. Soil often contains a high concentration of PCR inhibitors, but despite this all four toxin types were correctly identified in the soil samples (FIG. 4). None of the fecal samples gave a positive signal. In an attempt to determine if this was due to PCR inhibitors in the extracted samples, or if the DNA extraction process itself was inhibited, a small quantity of DNA was added to the extracted samples (1 μL of DNA at 10 ng μL-1 into 49 μL of each extracted sample). This yielded positive results for every toxin type (FIG. 5), indicating that PCR inhibitors were not interfering with the reaction, but rather the *C. botulinum* DNA was not being liberated from the inoculated bacteria during the extraction process when fecal material was present.

The assay provided herein detects DNA sequences that code for four botulinum toxin types rather than the presence of the toxin polypeptides themselves. In a natural disease outbreak situation organisms would likely be present with their toxin products. However, these DNA sequences may not be present in detectable amounts in highly purified toxin preparations such as those prepared for use as biological weapons.

Previous studies have described how certain strains of *C. botulinum* have the ability to produce two toxin types. Alternatively, an isolate may possess two types of toxin genes but only one toxin type will be expressed. Since this assay detects toxin gene sequences only, these organisms might produce positive results for both DNA sequences. Consequently, this assay correctly detects the capacity of *C. botulinum* to produce a specific toxin type.

Example 8

Confirmation and Validation of the Quadraplexed Assay

Several previously published assays were run on these isolates in order to confirm the results obtained by our qPCR assay. The qPCR assay described by Song et al. (2004) was used initially to confirm that all of these isolates were members of the genus Clostridium. The assay described by Lindstrom et al. (2001) was adapted to a real-time format and all isolates were also retested with this assay. The primer sequences employed were identical to those reported by Lindstrom et al. (2001). The primer sets were used as singleplex reactions by mixing one master mix bead, 500 nM of each of the forward and reverse primers, 1.25 μL of 20×SYBR Green, target DNA, and PCR-grade H2O to 25 μL. The reactions were then run in the SmartCycler II with the following cycling conditions: 95° C. for 2 min followed by 35 cycles of 95° C. for 25 s, 60° C. for 25 s and 72° C. for 60 s. The results indicated that in every case, the described quadraplexed assay detected the BoNT genes correctly.

To further confirm the quadraplexed assay, the real-time assay singleplex recently published by Fach et al. (2009) was used to determine the presence of single toxin genes. All primer and probe sequences used were as reported by Fach et al. (2009) as were the cycling conditions. All assays were performed on a Cepheid SmartCycler II. These results also matched perfectly with those of our described quadraplexed assay. Mouse bioassay information was gathered or produced for all isolates, as described above. In addition, MIDI fatty acid analysis identified all isolates as *C. botulinum*.

Example 9

Mouse Bioassay

Much of the mouse bioassay information was gathered from sources at ATCC, CDC and UDH. The information that could not be obtained from these sources was generated by performing the mouse bioassay on those isolates. Briefly, *C. botulinum* cultures were grown in Chopped Meat Medium (Anaerobe Systems, Morgan Hill, Calif.) for seven days. The liquid portion of the broth was removed to an Oakridge tube. An equal amount of cold Gelatin Diluent was added to the tube, which was vortexed. The tube was centrifuged at 15 000×g for 20 min at 4° C. The supernatant was removed and placed in a sterile screw cap tube. One mL aliquots of this solution were placed in separate tubes for toxin neutralization assays, which involved the addition of 0.25 mL of antitoxin to neurotoxin types A, B, E, or ABE antitoxin. One aliquot was left untreated. These mixtures of extract and antiserum were incubated at room temperature for 30-60 min. In addition, one aliquot was tested for heat lability. An aliquote of specimen was prepared for heat lability testing by placing approximately 1.2 mL of the extract in a sterile screw cap tube that was loosely capped. The tube was then heated in a boiling water bath for 10 min then allowed to return to room temperature.

Mice weighing 20 grams each were inoculated intraperitoneally with 0.5 mL of extract and observed for signs of botulism at 4, 8, 12, 24, 48, 72 and 96 hours post-injection. Botulinum toxin was considered present if samples of the raw extract caused symptoms of botulism followed by death when injected into mice, but did not cause symptoms of botulism or death when heated or mixed with one of the monovalent or trivalent antitoxins specific for the botulinum toxin involved.

Example 10

Specificity Testing

Figure 1A:
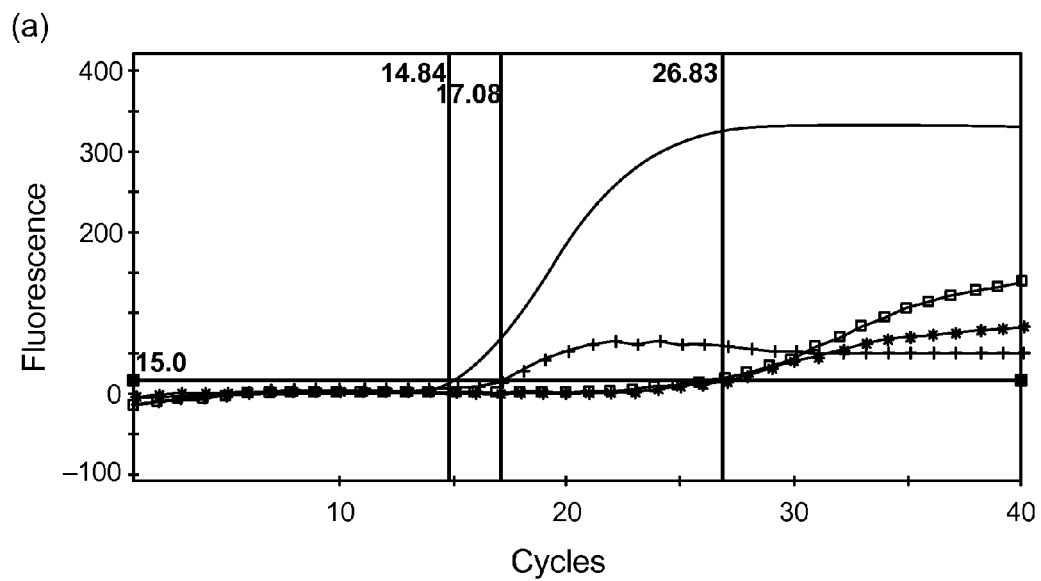
FIG. 1 depicts simultaneous detection of toxins A, B, E and F. (a) The quadruplex assay detected all four toxins concurrently. Toxin A (solid); toxin B (+); toxin E (square); toxin F (*). (b) Toxin types C (square and triangle) and D (circle) and near-neighbours (*C. argentinense*, diamond and asterisk; *C.*
Figure 1B:
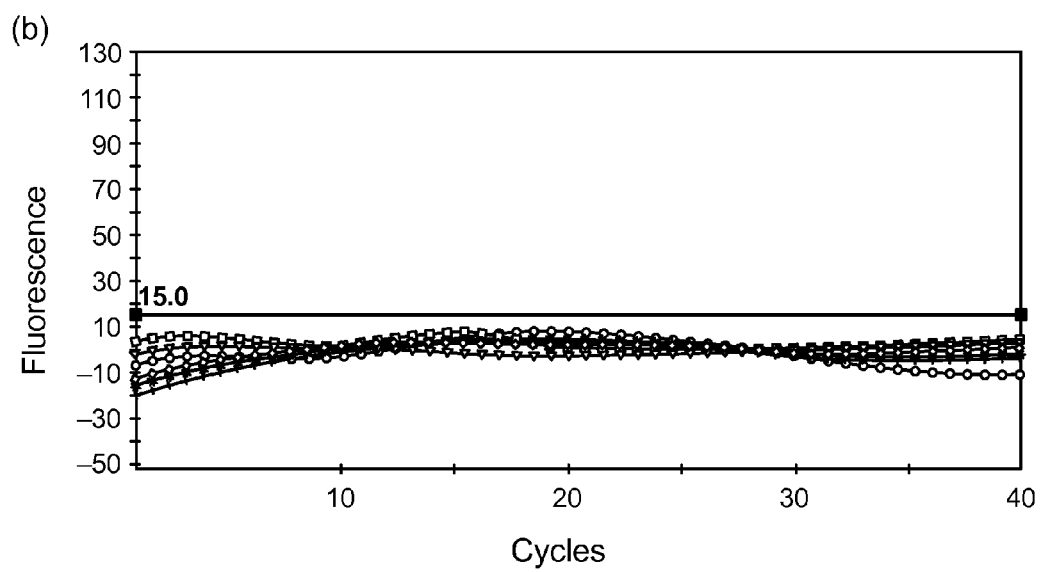
Figure 2A:
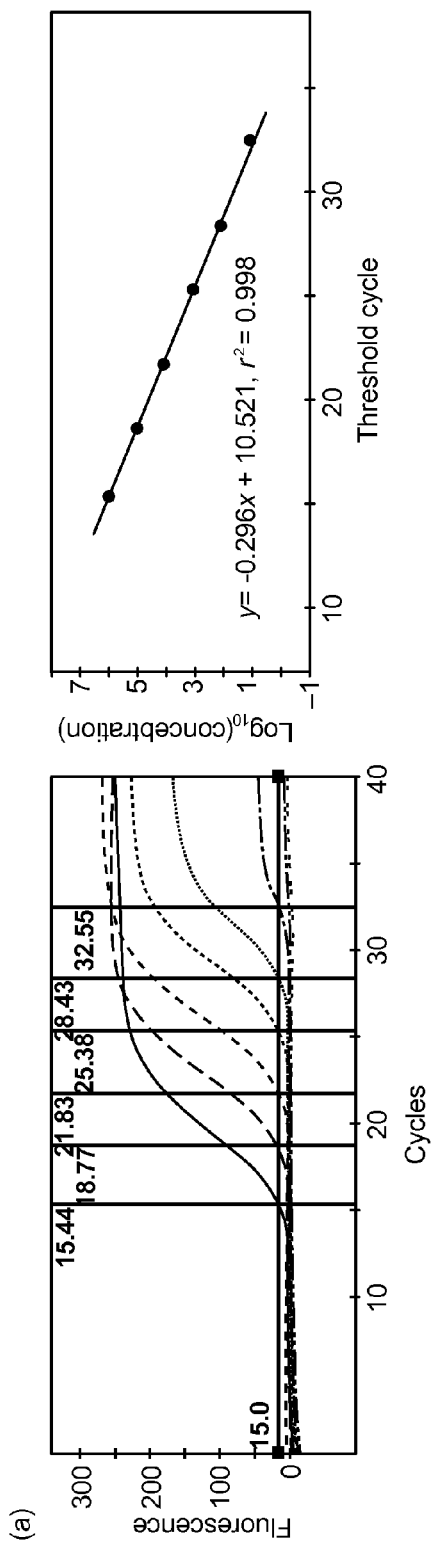
Figure 2B:
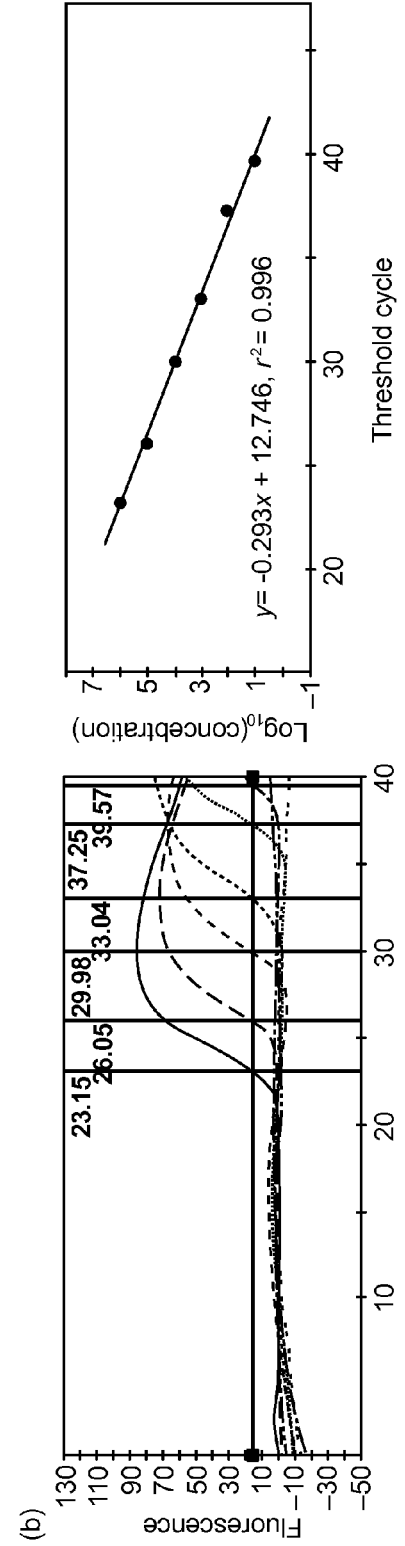
Figure 2C:
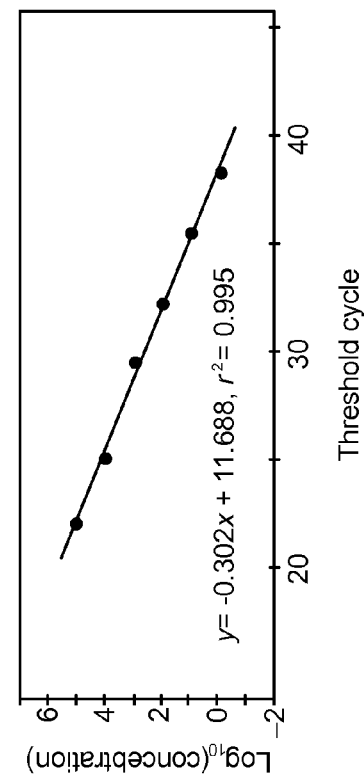
Figure 2C:
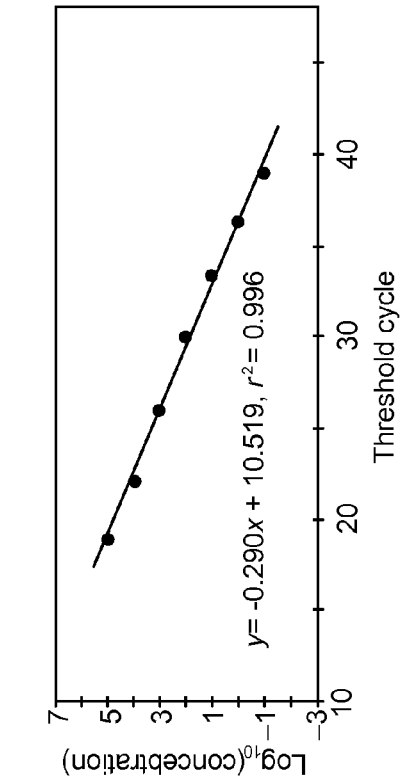
Figure 2D:
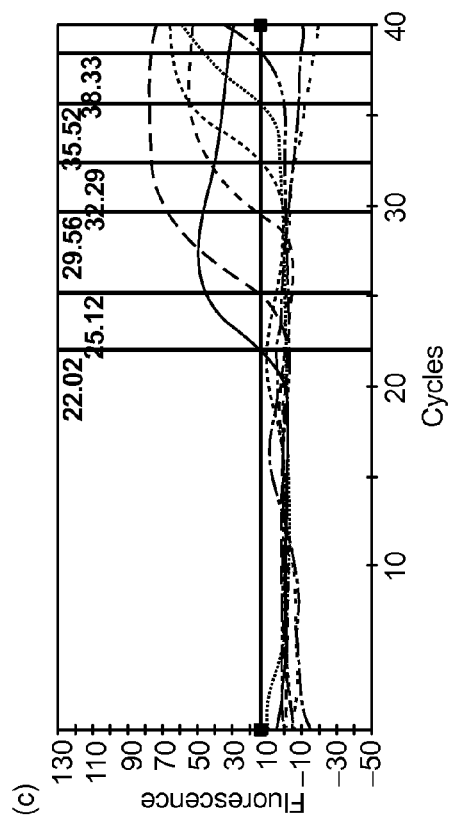
Figure 2D:
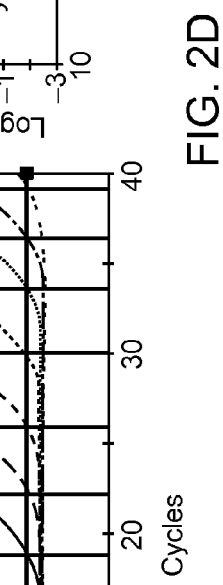
Figure 3A:
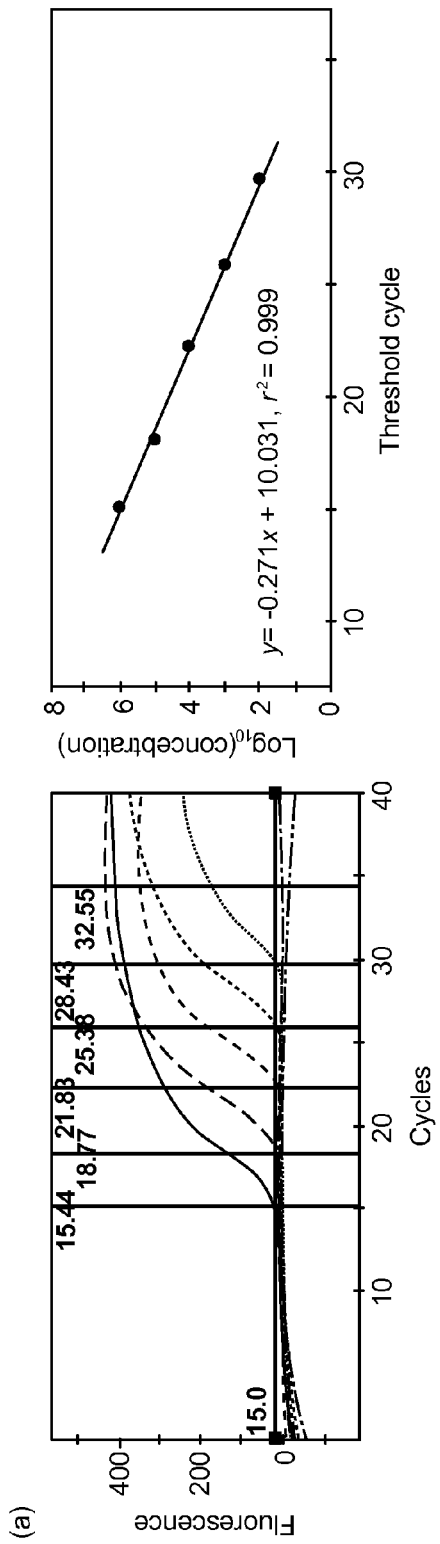
Figure 3B:
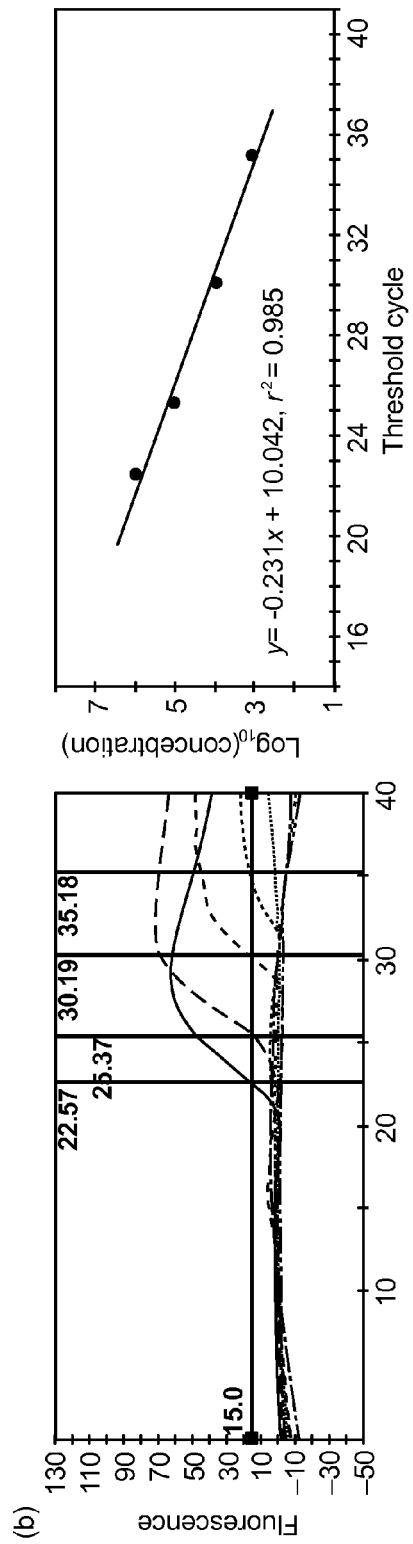
Figure 3C:
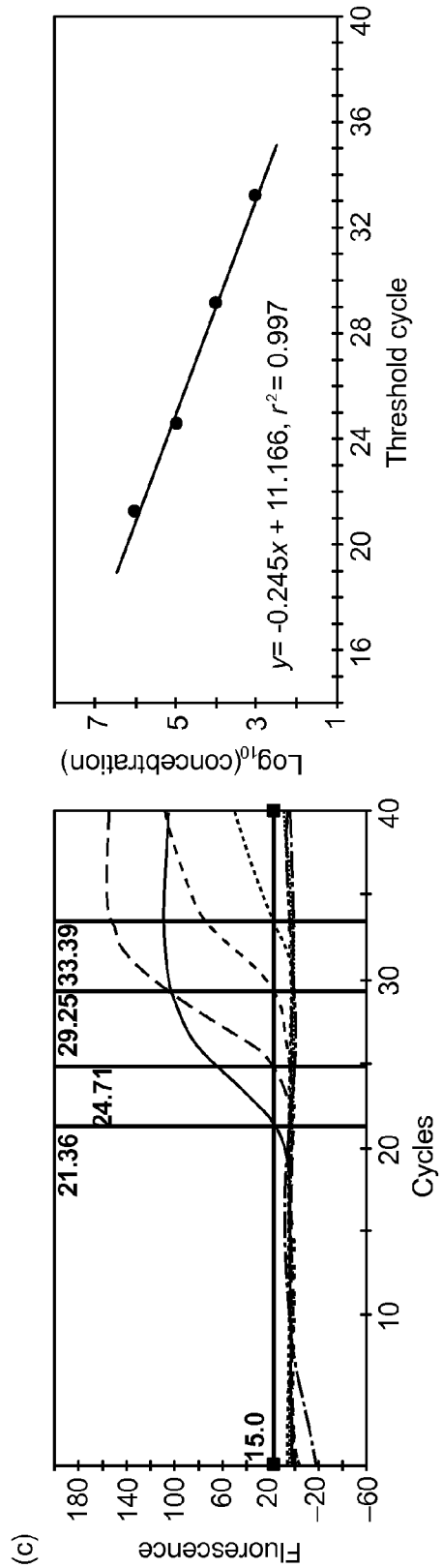
Figure 3D:
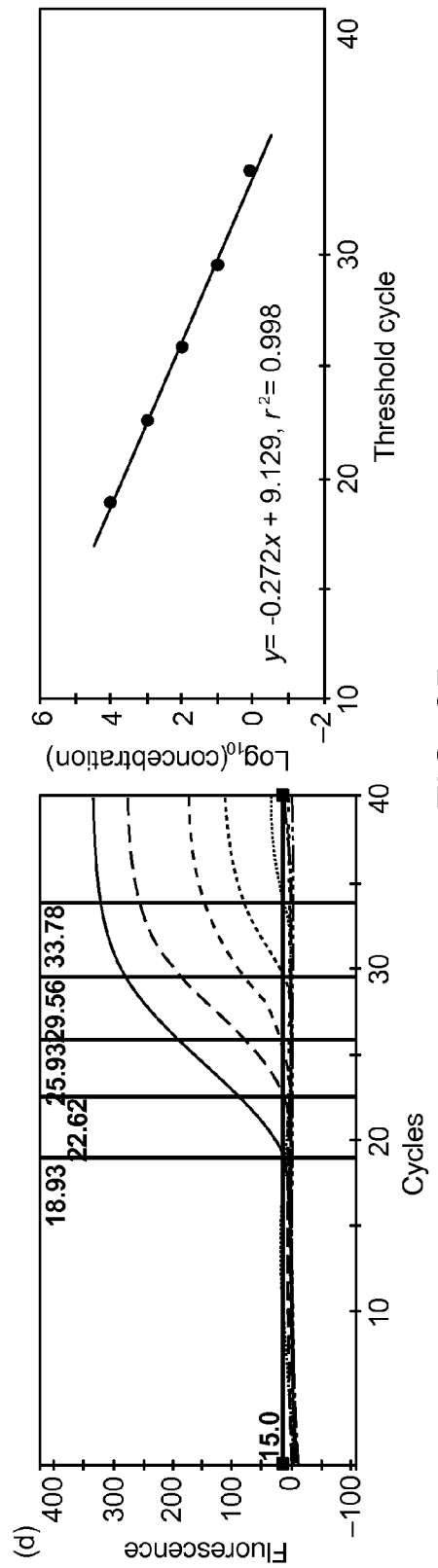
Figure 4A:
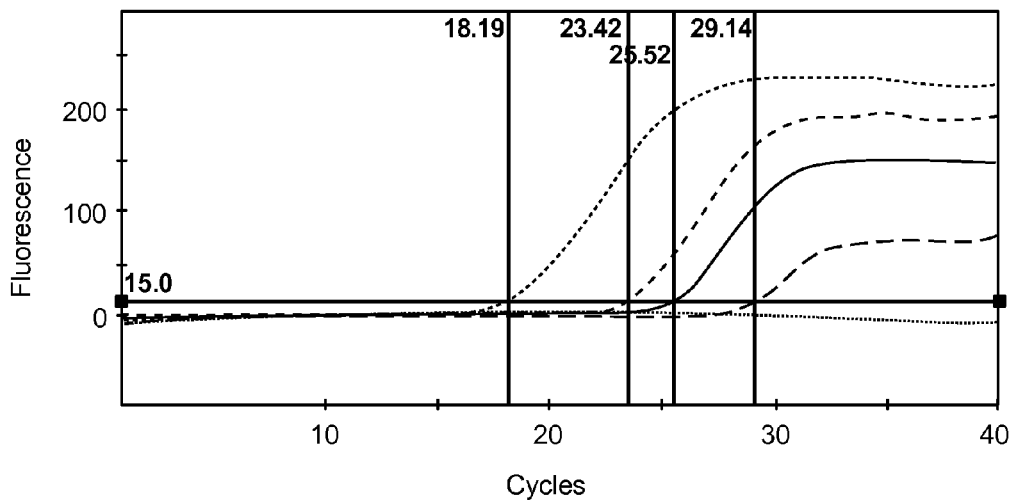
Figure 4B:
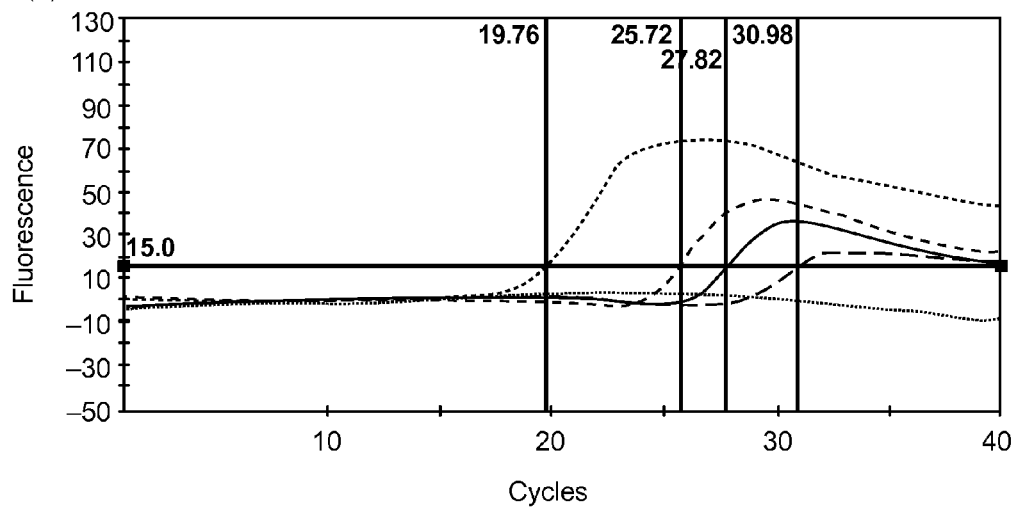
Figure 4C:
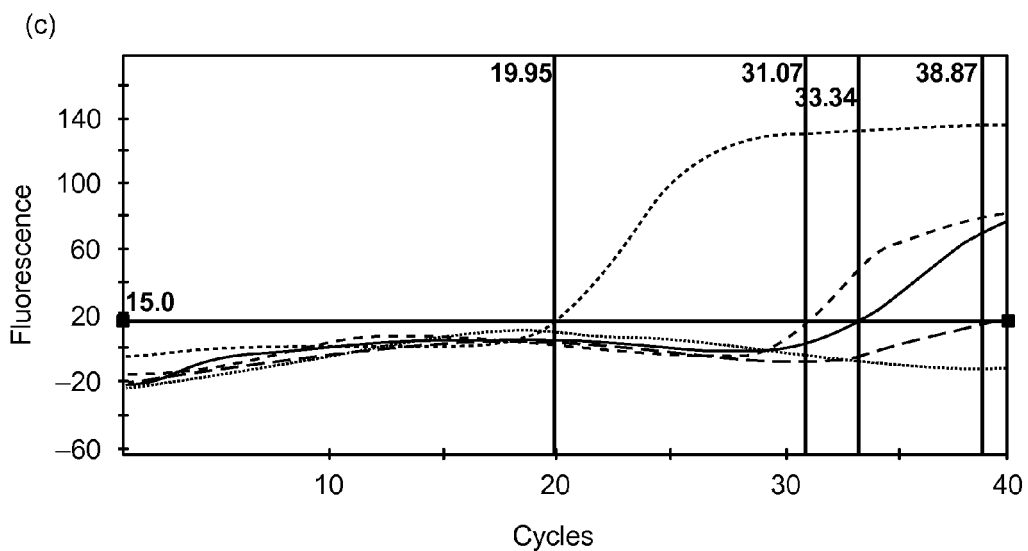
Figure 4D:
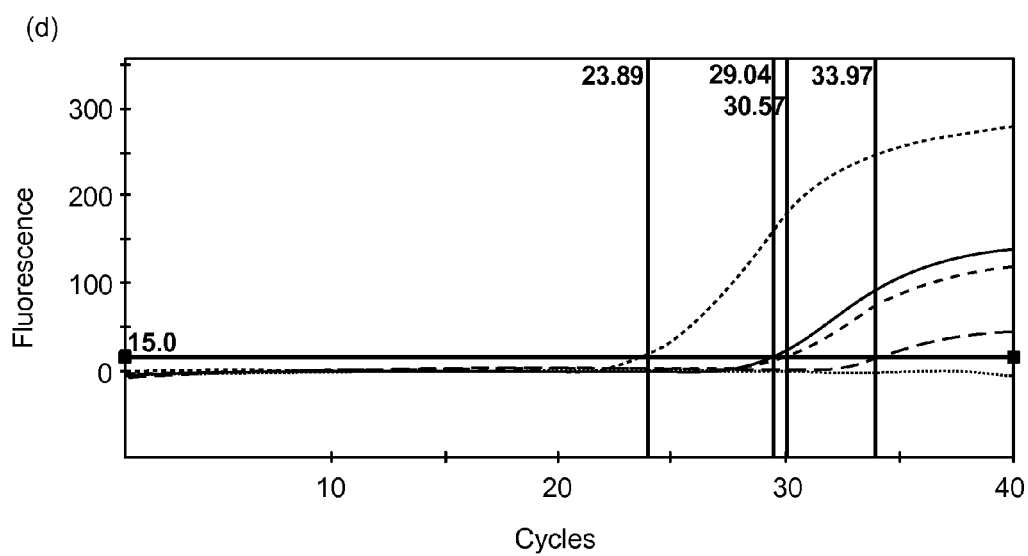

Initial specificity of each primer was evaluated in separate qPCR tubes using SYBR Green to detect amplification. Specific primers yielded threshold amplification in the presence of DNA for their respective toxin types, while maintaining a level non-amplification state when any other DNA was added. Having established that the primers were highly specific to their respective DNA targets, the SYBR Green was replaced with specific dual-labeled hydrolysis probes for toxin types A, B, E, and F. All isolates were tested a minimum of three times, and signal thresholds were exceeded only when specific primer and probe sets were used on target DNAs containing the corresponding toxin gene, indicating target specificity. When DNA from two, three, or four toxin types was combined, each toxin type produced a positive threshold signal. C. botulinum isolates containing the C or D toxin genes and near neighbors consistently produced a negative response on all dye channels (FIG. 1).

Of the 100 isolates examined in this study (Table 5), 79 were C. botulinum and tested positive for sequences corresponding to their respective toxin types (A, B, E or F). A total of 13 C. botulinum isolates producing the toxins C and D, which do not cause disease in humans, were also included as controls and always produced a negative result for the assay. Six Clostridial near-neighbor species tested negative for all four toxin types (Table 3).

Example 11

Sensitivity Testing

For each isolate, 10-fold serial dilutions were made of the purified genomic DNAs. For the singleplex assays, the threshold sensitivities for each toxin type were at least 13 fg for type A, 7.0 fg for type B, 8.4 fg for type E, and 8.4 fg for type F (FIG. 2). For the quadraplexed assay, the threshold sensitivities for each toxin type were at least 130 fg for type A, 700 fg for type B, 840 fg for type E, and 840 fg for type F (FIG. 3). This corresponds to a sensitivity of about 1-2 genome copies for the singleplex assays and 15-100 genome copies for the quadraplexed assay depending on toxin type.

Example 12

Toxin Type Variance from Those Purported

The isolates tested using the described assay represented a wide diversity with multiple isolates representing each of the A, B, C, D, E, and F toxin types. In most cases (59 of 72 isolates containing A, B, E or F toxin genes), the purported toxin type matched exactly that identified by the described assay. For seven isolates (CDC isolates 10305 T-5, 10306 A-2 and 10360 A-1 and UDH isolates 70200855, 70300379, 70401029 and 79002066), the mouse bioassay detected only the A toxin, whereas our assay detected the presence of both A and B toxin genes. The presence of genes for more than one toxin type, with only one type being expressed has been reported previously. This is likely the case for these isolates. There were also three isolates for which the assay results varied from the purported toxin type. The ATCC isolates 438 and 17786 were purported to produce toxin types B and E respectively, but our assay detected the gene for toxin type A in both iosolates. Mouse bioassay data on these cultures confirmed toxin type A for both of these isolates. The ATCC isolate 17845 was purported to have the B toxin gene, but no toxin genes were identified. This result was also confirmed by the mouse bioassay. It is possible that the toxin gene was contained on a plasmid that was lost during repeated culture.

Example 13

Sequence ID Numbers

TABLE 4

| SEQUENCE ID NUMBERS | | | |
|---|---|---|---|
| Target (gene) | Primer | Sequence (5' → 3') | SEQ ID No. |
| Toxin A | Forward | ACGCGAAATGGTTATGGYTCTACTC | 1 |
| | Reverse | GTGCTAATGYTACYGCTGGATCTG | 2 |
| Toxin B | Forward | AGTAATCCAGGAGAAGTGGAGCGA | 3 |
| | Reverse | CRAAGCCTTCCCTTGATGCAAA | 4 |
| Toxin E | Forward | CACAGAAAGTGCCCGAAGGTGAAA | 5 |
| | Reverse | GCTGCTTGCACAGGTTTATTGACA | 6 |
| Toxin F | Forward | GTGGAGGGMATMATAGTAGTACAGA | 7 |
| | Reverse | GGCTATCATAAGAGGTSCTYGCTTT | 8 |
| Toxin A | Probe | TGAGGAGTCACTTGAAGTTGATACAAATCC | 9 |
| Toxin B | Probe | CGCAAATTTAATAATATTTGGACCTGGGCC | 10 |
| Toxin E | Probe | GTCAATCTCACCTCTTCAATTGATACAGCA | 11 |
| Toxin F | Probe | AGCTCATGAATTGATACATGCACTGCA | 12 |

Example 14

Quadraplexed qPCR Assay for Individual Isolates

TABLE 4

Results of the quadraplexed qPCR assay for individual isolates

| Species | Isolate Number | Source | Purported Toxin Type | Mouse Bioassay Data | Detected Toxin Type | FAM Toxin A | Cy3 Toxin B | Cy5 Toxin E | Texas Red Toxin F |
|---|---|---|---|---|---|---|---|---|---|
| *C. botulinum* | 335 | UDH | A | A | A | + | − | − | − |
| *C. botulinum* | 438 | ATCC | B | A | A | + | − | − | − |
| *C. botulinum* | 439 | ATCC | B | B | B | − | + | − | − |
| *C. botulinum* | 3502 | ATCC | A | A | A | + | − | − | − |
| *C. botulinum* | 6060 | ATCC | C | C | | − | − | − | − |
| *C. botulinum* | 7948 | ATCC | A | A | A | + | − | − | − |
| *C. botulinum* | 7949 | ATCC | B | B | B | − | + | − | − |
| *C. botulinum* | 8083 | ATCC | B | B | B | − | + | − | − |
| *C. botulinum* | 9216 | CDC | B | B | B | − | + | − | − |
| *C. botulinum* | 9564 | ATCC | E | E | E | − | − | + | − |
| *C. botulinum* | 9633 | ATCC | D | D | | − | − | − | − |
| *C. botulinum* | 9691 | CDC | B | B | B | − | + | − | − |
| *C. botulinum* | 9948 | CDC | B | B | B | − | + | − | − |
| *C. botulinum* | 10305 T-5 | CDC | A | A | A & B | + | + | − | − |
| *C. botulinum* | 10306 A-2 | CDC | A | A | A & B | + | + | − | − |
| *C. botulinum* | 10360 A-1 | CDC | A | A | A & B | + | + | − | − |
| *C. botulinum* | 11772 | ATCC | C | C | | − | − | − | − |
| *C. botulinum* | 17782 | ATCC | C | C | | − | − | − | − |
| *C. botulinum* | 17783 | ATCC | B | B | B | − | + | − | − |
| *C. botulinum* | 17784 | ATCC | C | C | | − | − | − | − |
| *C. botulinum* | 17786 | ATCC | E | A | A | + | − | − | − |
| *C. botulinum* | 17841 | ATCC | B | B | B | − | + | − | − |
| *C. botulinum* | 17843 | ATCC | B | B | B | − | + | − | − |
| *C. botulinum* | 17844 | ATCC | B | B | B | − | + | − | − |
| *C. botulinum* | 17845 | ATCC | B | — | | − | − | − | − |
| *C. botulinum* | 17846 | ATCC | C | C | | − | − | − | − |
| *C. botulinum* | 17847 | ATCC | C | C | | − | − | − | − |
| *C. botulinum* | 17849 | ATCC | C | C | | − | − | − | − |
| *C. botulinum* | 17850 | ATCC | C | C | | − | − | − | − |
| *C. botulinum* | 17851 | ATCC | D | D | | − | − | − | − |
| *C. botulinum* | 17854 | ATCC | E | E | E | − | − | − | − |
| *C. botulinum* | 17862 | ATCC | A | A | A | + | − | − | − |
| *C. botulinum* | 23387 | ATCC | F | F | F | − | − | − | + |
| *C. botulinum* | 25763 | ATCC | A | A | A | + | − | − | − |
| *C. botulinum* | 25764 | ATCC | F | F | F | − | − | − | + |
| *C. botulinum* | 25765 | ATCC | B | B | B | − | + | − | − |
| *C. botulinum* | 25766 | ATCC | C | C | | − | − | − | − |
| *C. botulinum* | 27321 | ATCC | F | F | F | − | − | − | + |
| *C. botulinum* | 27517 | ATCC | D | D | | − | − | − | − |
| *C. botulinum* | 35415 | ATCC | F | F | F | − | − | − | + |
| *C. botulinum* | 43757 | ATCC | B & F | B & F | B & F | − | + | − | + |
| *C. botulinum* | 43758 | ATCC | B & F | B & F | B & F | − | + | − | + |
| *C. botulinum* | 51385 | ATCC | A | A | A | + | − | − | − |
| *C. botulinum* | 51386 | ATCC | B | B | B | − | + | − | − |
| *C. botulinum* | 51387 | ATCC | B | B | B | − | + | − | − |
| *C. botulinum* | 49050206 | CDC | E | E | E | − | − | + | − |
| *C. botulinum* | 52040208 | CDC | — | A | A & E | + | − | + | − |
| *C. botulinum* | 57020620 | CDC | — | A | A & E | + | − | + | − |
| *C. botulinum* | 70000545a | UDH | A | A | A | + | − | − | − |
| *C. botulinum* | 70000545b | UDH | A | A | A | + | − | − | − |
| *C. botulinum* | 70000787 | UDH | A | A | A | + | − | − | − |
| *C. botulinum* | 70000831 | UDH | A | A | A | + | − | − | − |
| *C. botulinum* | 70000875 | UDH | A | A | A | + | − | − | − |
| *C. botulinum* | 70001117 | UDH | A | A | A | + | − | − | − |
| *C. botulinum* | 70001227 | UDH | A | A | A | + | − | − | − |
| *C. botulinum* | 70002286 | UDH | A | A | A | + | − | − | − |
| *C. botulinum* | 70002773 | UDH | A | A | A | + | − | − | − |
| *C. botulinum* | 70100222 | UDH | A | A | A | + | − | − | − |
| *C. botulinum* | 70100352 | UDH | A | A | A | + | − | − | − |
| *C. botulinum* | 70101284 | UDH | A | A | A | + | − | − | − |
| *C. botulinum* | 70101393 | UDH | A | A | A | + | − | − | − |
| *C. botulinum* | 70101439 | UDH | A | A | A | + | − | − | − |
| *C. botulinum* | 70200855 | UDH | A | A | A & B | + | + | − | − |
| *C. botulinum* | 70201813 | UDH | A | A | A | + | − | − | − |
| *C. botulinum* | 70300023 | UDH | A | A | A | + | − | − | − |
| *C. botulinum* | 70300141 | UDH | A | A | A | + | − | − | − |
| *C. botulinum* | 70300167 | UDH | A | A | A | + | − | − | − |
| *C. botulinum* | 70300294 | UDH | A | A | A | + | − | − | − |

TABLE 4-continued

Results of the quadraplexed qPCR assay for individual isolates

| Species | Isolate Number | Source | Purported Toxin Type | Mouse Bioassay Data | Detected Toxin Type | FAM Toxin A | Cy3 Toxin B | Cy5 Toxin E | Texas Red Toxin F |
|---|---|---|---|---|---|---|---|---|---|
| C. botulinum | 70300379 | UDH | A | A | A & B | + | + | − | − |
| C. botulinum | 70301012 | UDH | A | A | A | + | − | − | − |
| C. botulinum | 70400119 | UDH | A | A | A | + | − | − | − |
| C. botulinum | 70400126 | UDH | A | A | A | + | − | − | − |
| C. botulinum | 70400766 | UDH | A | A | A | + | − | − | − |
| C. botulinum | 70401029 | UDH | A | A | A & B | + | + | − | − |
| C. botulinum | 70500301 | UDH | A | A | A | + | − | − | − |
| C. botulinum | 79002066 | UDH | A | A | A & B | + | + | − | − |
| C. botulinum | 79103053 | UDH | A | A | A | + | − | − | − |
| C. botulinum | 79900618 | UDH | A | A | A | + | − | − | − |
| C. botulinum | 79900698 | UDH | A | A | A | + | − | − | − |
| C. botulinum | 90300114 | UDH | A | A | A | + | − | − | − |
| C. botulinum | B CN2-5.2 | Batelle | — | B | B | − | + | − | − |
| C. argentinense | 27322 | ATCC | | | | − | − | − | − |
| C. argentinense | 33263 | ATCC | | | | − | − | − | − |
| C. beijernckii | 25752 | ATCC | | | | − | − | − | − |
| C. haemolyticum | 9650 | ATCC | | | | − | − | − | − |
| C. perfringens | 13124 | ATCC | | | | − | − | − | − |
| C. subterminale | 25774 | ATCC | | | | − | − | − | − |
| B. anthracis | A0156 | LSU | | | | − | − | − | − |
| B. abortus | 772 | NADC | | | | − | − | − | − |
| E. coli | 11229 | ATCC | | | | − | − | − | − |
| F. tularensis | 80606984 | UDH | | | | − | − | − | − |
| L. monocytogenes | 15313 | ATCC | | | | − | − | − | − |
| P. aeurginosa | 15442 | ATCC | | | | − | − | − | − |
| S. aureus | 6538 | ATCC | | | | − | − | − | − |
| S. pneumoniae | 49619 | ATCC | | | | − | − | − | − |
| S. pyogenes | 14289 | ATCC | | | | − | − | − | − |
| V. cholerae | 14035 | ATCC | | | | − | − | − | − |
| Y. pestis | 4766 | NMDH | | | | − | − | − | − |

LSU, Louisiana State University;
NADC, National Animal Disease Center;
NMDH, New Mexico Department of Health Embodiments of the method provided herein are set forth in the claims that follow.

---

What is claimed is:

1. A multiplexing reaction method for detecting the presence or absence of at least one of Clostridium botulinum toxin gene A, B, E, and F in a biological sample, the method comprising:
   a. preparing a nucleic acid mixture comprising DNA from the biological sample;
   b. providing a purified polynucleic acid primer having at least 90% sequence homology to SEQ ID NO:2 and at least one isolated and purified polynucleic acid primer pair configured for use in at least one of a PCR or other amplification reaction and selected from the group consisting of sequences having at least 90% sequence homology to SEQ ID NOS: 1, 3-4, 5-6, and 7-8;
   c. providing at least one polynucleic acid probe selected from the group consisting of sequences having at least 90% sequence homology SEQ ID NOS 9, 10, 11, and 12, wherein each probe is labeled with a different detectable label;
   d. conducting an amplification reaction with a DNA polymerase using the mixture; and
   e. detecting hybridization of any of the at least one probe to the amplification product of step d. wherein detection is one of real time detection and delayed detection and wherein hybridization indicates the presence of at least one of toxin genes A, B, E, or F in the biological sample.

2. The method of claim 1, wherein said detectable label is a fluorescent label.

3. The method of claim 1, wherein said detectable label is selected from the group consisting of FAM, Cy3, Cy5 and Texas Red (TexR).

4. The method of claim 1, wherein a signal from at least two detectable labels is displayed simultaneously on at least two optical channels.

5. The method of claim 1, wherein the sample is from a mammal.

6. The method of claim 5, wherein the sample is selected from the group consisting of serum, secretion, emesis, wound, tissue, blood, fluid, and feces.

7. The method of claim 6, wherein the sample is from a human.

8. The method of claim 1, wherein the sample is vegetative matter.

9. The method of claim 1, wherein the sample is one of a food product or medicant suitable for ingestion by an animal.

10. The method of claim 1, wherein the sample is one of a food product or medicant suitable for ingestion by a human.

11. The method of claim 9, wherein the sample comprises a public food supply.

12. The method of claim 11, further comprising issuing a public health advisory based on a result positive for at least one of C. botulinum toxin gene A, B, E, and F.

13. The method of claim 1 further comprising diagnosing C. botulinum in a human by determining the presence or absence of at least one C. botulinum toxin gene in a sample from a human according claim 7, and correlating the presence or absence the C. botulinum toxin gene in the sample with the diagnosis of the human as being one of infected or not infected with C. botulinum.

14. The method of claim 13 further comprising administering C. botulinum anti-toxin effective against at least one toxin produced by the at least one identified C. botulinum toxin gene.

15. A composition for detecting multiple botulinum toxin groups in a multiplexing reaction, the composition comprising:
   a. an isolated and purified polynucleic acid primer configured to function in at least one of a PCR and other amplification reaction and having at least 90% sequence homology to GTGCTAATGYTACYGCTGGATCTG (SEQ ID NO:2) and at least one isolated and purified polynucleic acid primer configured to function in at least one of a PCR and other amplification reaction and having at least 90% sequence homology to the sequence of at least one of ACGCGAAATGGTTATGGYTCTACTC (SEQ ID NO:1), AGTAATCCAGGAGAAGTGGAGCGA (SEQ ID NO:3), CRAAGCCTTCCCTTGATGCAAA (SEQ ID NO:4), CACAGAAAGTGCCCGAAGGTGAAA (SEQ ID NO:5), GCTGCTTGCACAGGTTTATTGACA (SEQ ID NO:6), GTGGAGGGMATMATAGTAGTACAGA (SEQ ID NO:7), and GGCTATCATAAGAGGTSCTYGCTTT (SEQ ID NO:8), wherein Y represents at least one of T and C, M represents at least one of A and C, R represents at least one of A and G, and S represents at least one of C and G.

16. The composition according to claim 15, further comprising at least one polynucleic acid probe labeled with a detectable label and having at least 90% sequence homology to at least one of TGAGGAGTCACTTGAAGTTGATACAAATCC (SEQ ID NO:9), CGCAAATTTAATAATATTTGGACCTGGGCC (SEQ ID NO:10), GTCAATCTCACCTCTTCAATTGATACAGCA (SEQ ID NO:11), AGCTCATGAATTGATACATGCACTGCA (SEQ ID NO:12).

17. A kit for detecting the presence of at least one of Clostridium botulinum toxin genes A, B, E, and F in a biological sample, the kit comprising:
   a. an isolated and purified polynucleic acid primer configured for use in a PCR reaction and having at least 90% sequence homology to SEQ ID NO:2;
   b. at least one isolated and purfied polynucleic acid primer configured for use in a PCR reaction and having least 90% sequence homology to a sequence selected from the group consisting of SEQ ID NOS: 1, 3-4, 5-6, and 7-8; and c. at least one polynucleic acid probe having at least 90% sequence homology to a sequence selected from the group consisting of SEQ ID NOS: 9, 10, 11, and 12 wherein each probe is labeled with a different detectable label.

18. The kit of claim 17, further comprising instructions for performing the assay.

19. The kit of claim 18, further comprising reaction reagents.

20. The composition according to claim 15 further comprising a plurality of primers such that each possible Y nucleic acid variation for SEQ ID NO:1 is represented by at least one primer, each possible combination of Y nucleic acid variations for SEQ ID NO:2 is represented by at least one primer, each possible R nucleic acid variation for SEQ ID NO:4 is represented by at least one primer, each possible combination of M nucleic acid variations for SEQ ID NO: 7 is represented by at least one primer and each possible combination of S and Y nucleic acid variations for SEQ ID NO:8 is represented by at least one primer.

21. The composition according to claim 20 wherein within each SEQ ID NO the applicable Y, M, R, and S primer variations are present in equal molar amounts.

22. The composition according to claim 20 wherein a primer and probe for Botulinum toxin type A is present in a higher molar amount than a primer and probe for at least one of Botulinum toxin type B, E, and F.

23. The method according to claim 1 further comprising providing a plurality of primers such that each possible Y nucleic acid variation for SEQ ID NO:1 is represented by at least one primer, each possible combination of Y nucleic acid variations for SEQ ID NO:2 is represented by at least one primer, each possible R nucleic acid variation for SEQ ID NO; 4 is represented by at least one primer, each possible combination of M nucleic acid variations for SEQ ID NO: 7 is represented by at least one primer and each possible combination of S and Y nucleic acid variations for SEQ ID NO:8 is represented by at least one primer.

24. A method according to claim 23, wherein within each SEQ ID NO the applicable primers representing the Y, M, R, and S variations are provided in an equal molar amount.

25. The method according to claim 23 wherein a primer and probe for Botulinum toxin type A is provided in a higher molar amount than a primer and probe for at least one of Botulinum toxin type B, E, and F.

26. The composition of claim 16, wherein the label is a fluorescent label.

27. The composition of claim 16, wherein the label comprises at least one of FAM, Cy3, Cy5 and Texas Red (TexR).

* * * * *